United States Patent [19]

Rada

[11] Patent Number: 5,628,197

[45] Date of Patent: May 13, 1997

[54] TISSUE FREEZING APPARATUS

[76] Inventor: David C. Rada, 248 Lake Shore West, Lake Quivira, Kans. 66106

[21] Appl. No.: 531,719

[22] Filed: Sep. 21, 1995

[51] Int. Cl.$^6$ ............................ F25D 25/00; B25B 11/00
[52] U.S. Cl. ................................. 62/62; 62/341; 269/21; 83/915.5
[58] Field of Search .................................. 62/62, 64, 340, 62/341, 383, 378; 269/21; 83/915.5

[56] References Cited

U.S. PATENT DOCUMENTS

| | | |
|---|---|---|
| 3,209,821 | 10/1965 | Zeytoonian ............................... 62/341 |
| 3,218,896 | 11/1965 | McCormick . |
| 3,296,821 | 1/1967 | Malinin ................................. 62/341 |
| 3,520,055 | 7/1970 | Jannett . |
| 3,598,006 | 8/1971 | Gerber . |
| 3,654,019 | 4/1972 | Cusik . |
| 3,667,330 | 6/1972 | Kobernick . |
| 3,737,335 | 6/1973 | Feinberg . |
| 3,742,802 | 7/1973 | Maerz . |
| 3,744,262 | 7/1973 | Bose ...................................... 62/62 |
| 3,765,289 | 10/1973 | Gerber et al. . |
| 3,803,958 | 4/1974 | Fernandez-Moran . |
| 3,832,923 | 9/1974 | Lassmann et al. . |
| 4,012,475 | 3/1977 | Kindel . |
| 4,060,440 | 11/1977 | Behme . |
| 4,190,472 | 2/1980 | Slonicki . |
| 4,532,838 | 8/1985 | Söderkvist . |
| 4,543,862 | 10/1985 | Levene . |
| 4,545,831 | 10/1985 | Ornstein . |
| 4,695,339 | 9/1987 | Rada . |
| 4,751,828 | 6/1988 | Coulter et al. .............................. 62/62 |
| 4,752,347 | 6/1988 | Rada ...................................... 156/382 |

OTHER PUBLICATIONS

Evaluation of a Method for Controlled Tissue Embedding for Histologic Evaluation of Tumor Margins; Daniel E. Gormley, M.D.; *The American Journal of Dermatopathology;* 9(4); 308–315, 1987.

Chemosurgical Reports: Frozen–Section Processing with the Miami Special; C. William Hanke, M.D. et al.; *J. Dermatol. Surg. Oncol.* 9:4 Apr. 1983.

Mohs Surgery; Neil A. Swanson, M.D.; *Arch Dermatol*—vol. 119, Sep. 1983.

A New Method for Preparing Tissue Blocks for Cryostat Sectioning; Vernon H. Carter, M.D.; *J. Dermatol. Surg. Oncol.* 11:7 Jul. 1985.

How to Prepare Tissue Blocks; Justo Concepcion; (published as Letter to the Editor), *J. Dermatol. Surg. Oncol.* 12:2 Feb. 1986.

Technical Procedures for Mohs Fresh Surgery; Ana Maria Picoto Antonio Picoto, M.D.; *J. Dermatol. Surg. Oncol.* 12:2 Feb. 1986.

*Primary Examiner*—William Doerrler
*Attorney, Agent, or Firm*—Litman, McMahon and Brown, L.L.C.

[57] ABSTRACT

An apparatus for quick freezing tissue specimens includes a base supporting a linear motion platform and a rotational motion platform. Each of the platforms includes a plurality of discs for covering and receiving respectfully specimen to be frozen. Each of the discs includes a chambers positioned to very quickly and rapidly disperse cryogenic fluid therein and convey away evaporated gases therefrom. The discs are flow connect to a cryogenic fluid source such as a liquid nitrogen tank and a vacuum is drawn on the gaseous side system by a vacuum pump. The discharge of the vacuum pump is returned to the cryogenic tank such that the vacuum pump both draws the cryogenic fluid through the system and pressurizes the tank so as to motivate the fluid through the system. A rotational column with a cryogenic junction conveys the cryogenic fluid to and from the platform that rotates. The junction is constructed of axially connected and rotatable quartz tubing. A plurality of channels encircle each disc and are connected to a vacuum system. A latch and trigger mechanism allows the rotatable platform to swing about an axis in an angular motion and thereafter stop, thereafter the linear platform moves linearly toward the rotational platform. The linear platform is reset by rotation of the rotational platform.

52 Claims, 7 Drawing Sheets

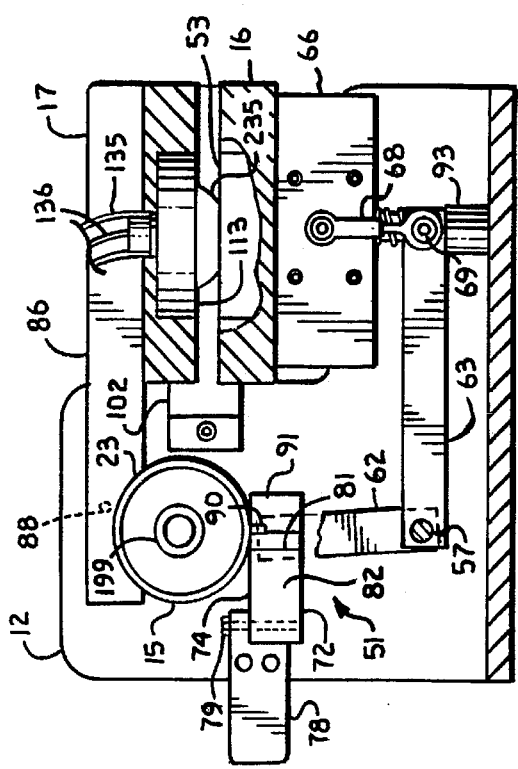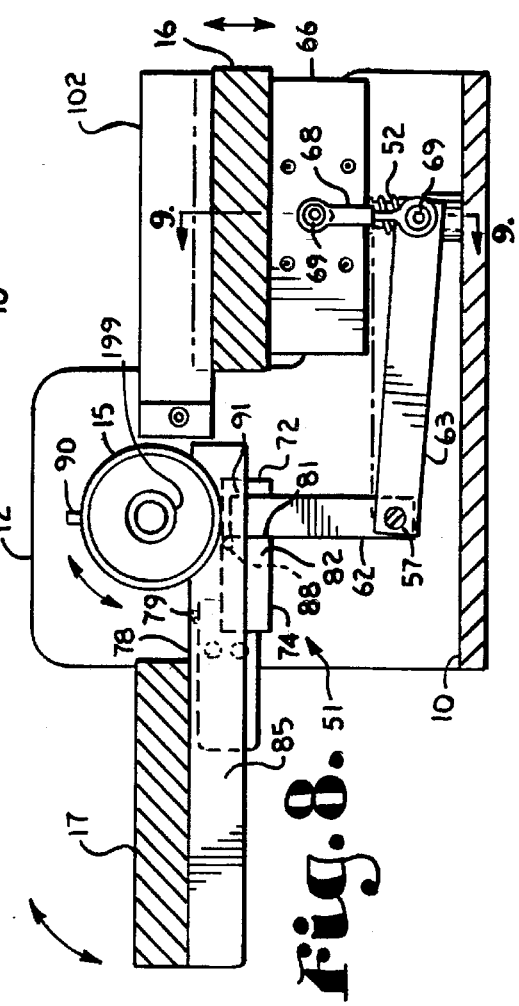

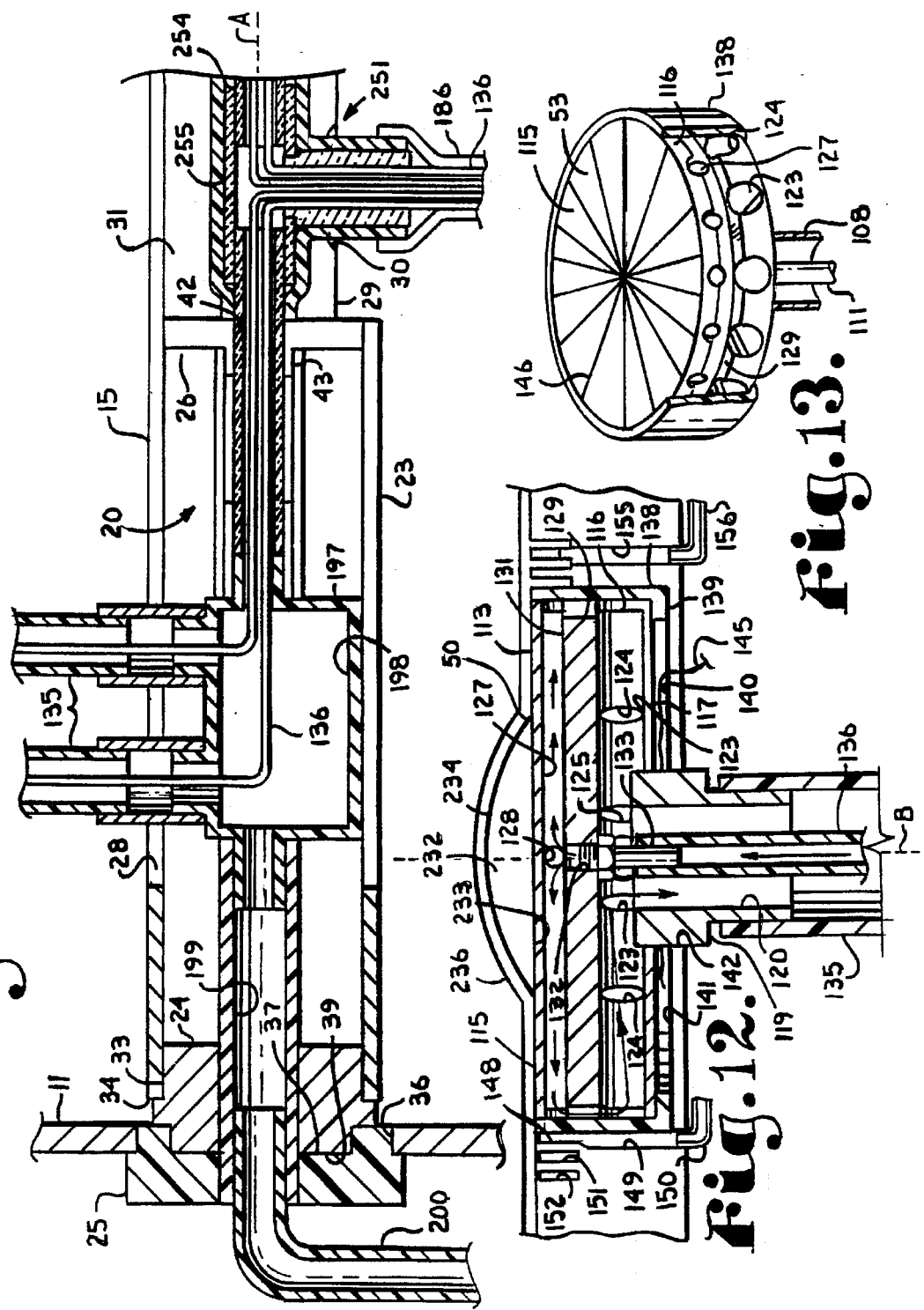

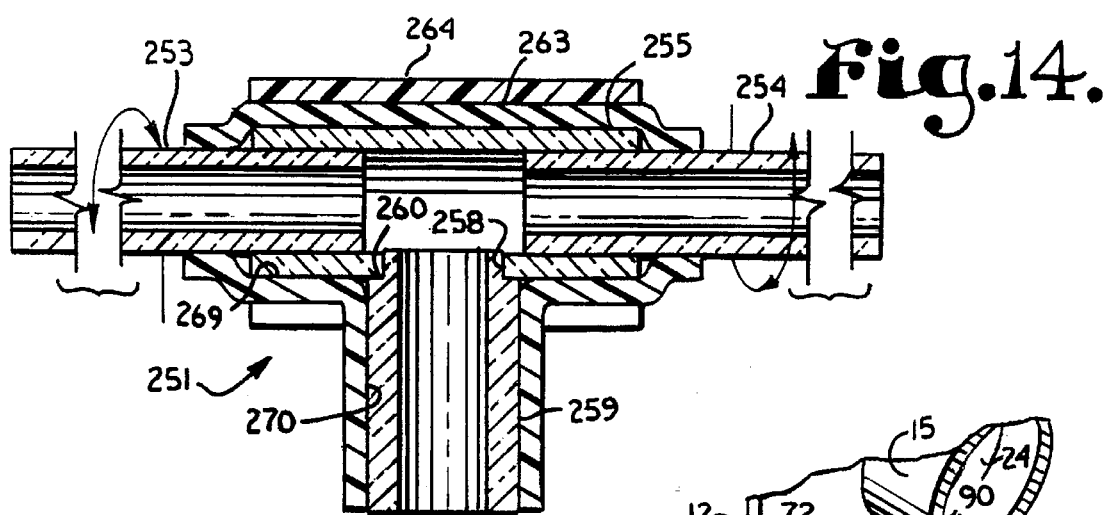
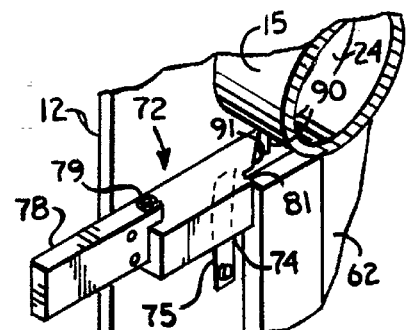
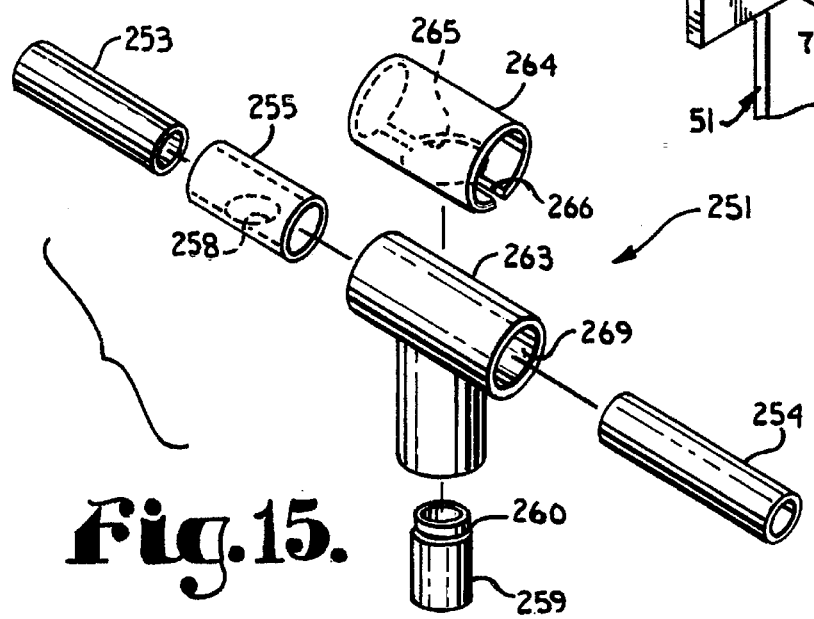

TISSUE FREEZING APPARATUS

BACKGROUND OF THE INVENTION

The present application is directed to an apparatus for rapidly freezing tissue specimens with cryogenic fluids, especially liquid nitrogen.

In many types of medical procedures, tissue specimens are removed from living persons and studied. Quite frequently these tissue specimens include a cancerous tumor (neoplasm) or other unwanted localized growth and it is the desire of the medical procedure to ensure that this tumor or growth is entirely excised from the person during the procedure. In order to ensure that the tissue associated with the tumor or other unwanted growth is completely removed, the exterior of the removed section is carefully microscopically studied in order to determine whether there is only good tissue or whether unwanted tissue is present. In this way, a physician can determine, for example, if there is a portion of a tumor that has been left within the good living tissue. If this occurs, the physician removes another deeper layer of the good tissue and again performs the procedure.

In order to best study the exterior layer and deeper layers of the tissue specimen, the specimen is preferably placed in a configuration wherein the deepest layer of the specimen is flattened and very thin slices of the tissue (normally about 5 to 7 micrometers in thickness) are then removed and studied. This is accomplished by use of a microtome or cryostat. In order to effectively slice the tissue in relatively very fine layers, the tissue must be firm and is preferably frozen to allow the thin slicing. Various devices have been provided in the prior art for flattening and hardening tissue samples for this purpose. As an example my previous two U.S. Pat. Nos. 4,695,339 and 4,752,347 have described various devices and methods for this purpose. My previous two patents further describe certain aspects of the process and needed apparatus that may be useful in conjunction with the present invention and are both incorporated herein by reference.

One of the main problem associated with the process of preparing tissue specimens for study is time. It normally takes a substantial period of time to freeze a fairly thick tissue specimen and during this entire period the patient from whom the specimen was removed must wait to determine if a further specimen must be removed and tested. This may go on for some lengthy period of time and is obviously uncomfortable to the patient. It also takes a substantial period of the physician's time to wait for the specimens to cool to a temperature that allows for slicing and microscopic review. Consequently, it is extremely important to be able to freeze the tissue samples as quickly as possible. The apparatus of the present invention has a number of improvements which are specifically designed to very quickly and rapidly freeze the specimen so there is only a very minimal amount of time spent waiting for the freezing procedure to occur.

It is also noted that the time factor is important with respect to the quality of the specimen produced. Very fast deep freezing techniques (sometimes referred to as "snap" freezing) produce less histologic artifact in the specimen. In particular, the quick freezing produces fewer large water crystals.

A second problem associated with the devices of the prior art is also indirectly related to time. In order to freeze a specimen quickest, the inventor has found it best to simultaneously cool a specimen from opposite sides thereof as compared to applying a device of comparatively low temperature (cold sink) to cool from only one side of the specimen. In this way heat migrates in two directions rather than in just one and substantially reduces the amount of time needed to freeze a specimen up to 50% of applying cold sink to just one side thereof.

As has been noted above, it is also important that the specimen have a very flat profile with respect to the under side that is to be inspected to make sure that it is all non tumor tissue. This flat profile helps to ensure that when a very thin slice is taken that the entire lower surface of the specimen will be sampled by the slice. When the specimen is placed on a first surface and flattened, that surface can then function as a first cold sink in accordance with the present invention. Unfortunately, when a second surface is applied to the opposite side of the specimen to function as a second cold sink, any lateral or sideways movement of the second surface will cause the specimen to roll slightly and may unflatten certain edges of the specimen thereby leading to an unsatisfactory first slice.

Therefore it is important to provide an apparatus wherein, not only can a second cold sink be placed adjacent to the specimen to reduce freezing time of the specimen, but also it is necessary to ensure that the second sink move only linearly toward the specimen with substantially no sideways or angular motion. The apparatus of the present invention is designed to provide a cold sink to both sides of the specimen while maintaining the underside surface of the specimen as flat as possible.

In order to most advantageously ensure that the upper and lower surfaces that operably function as cold sinks are aligned when brought together, the two surfaces are connected to plates or platforms which are hinged relative to one another so that at least one is swingable about an arc. This allows an operator to pivot or swing one plate away from the other so as to allow access to a receiving surface for placing the specimen thereon and then again after the specimen is frozen. Although the swinging of at least one plate relative to the other allows for proper registration of the two plates once they are positioned one above the other, this does present some problems, one of which has been discussed before.

In particular, it is important that the specimen not be moved laterally during positioning of the second plate over the first plate. Consequently, the apparatus is provided with structure which allows the specimen to be placed on the receiving surface of one of the plates and then at least one of the plates is swung to a position over the other plate. In this manner there is a rotating plate that has a rotational movement associated therewith. Once positioned in spaced but facing relationship, the two plates are moved linearly relative to one another such that as the two plates move toward one another there is essentially very little or no laterally movement between the surfaces that receive and cover the specimen. This reduces the likelihood that any of the peripheria or margin of the specimen which engages the receiving surface will be peeled up or rolled back from that surface.

Another problem associated with this system is related to the cooperation of the rotary movement with a cryogenic system. In particular, in order to provide quick freezing of the specimen, cryogenic fluid is provided to both of the plates so as to very quickly cool the surfaces both receiving and covering the specimen (as well as the surfaces related supporting structure) and in turn freeze the specimen.

A cryogenic fluid, preferably liquid nitrogen, at relatively very low temperatures is utilized to relatively quickly cool the surfaces receiving and covering the specimen. Transfer of the cryogenic fluid to the rotating plate to cool the surface associated therewith presents somewhat of a problem from an engineering point of view in that care must be taken to both support and contain the cryogenic fluid, which requires tubing for the cryogenic fluid to pass through a junction associated with the hinge of the rotating plate, and be distributed from there to the rotating plate beneath the surface associated therewith.

The cryogenic fluid tubing must be fairly stable and a structure must be provided to protect it. However, the cryogenic fluid also has the property of freezing (so that the pivot portions of the hinge can not pivot) or at least warping many of the conventional materials of construction that have a tendency to elongate or shorten with the substantial cooling encountered with the cryogenic fluids so that the hinge of the rotating plate becomes nonfunctional if constructed conventionally. Therefore, it is necessary to also provide a hinge which functions effectively in conjunction with cryogenic fluids.

The hinge is provided by means of interlocking quartz tubular members which remain rotatable relative to one another even with the extreme cooling associated with the cryogenic fluids. The quartz tubes neither freeze together or suffer dimensional changes that would effect and possibly lock up other materials.

Furthermore, in order to reduce the amount of time needed to freeze a sample, improvements were also desirable in the distribution of the cryogenic fluid. In particular, the cryogenic fluid is distributed to support structure in the plates beneath the surfaces that receive and cover the specimen so as to very rapidly cool those surfaces and in turn cool the specimen. A disc was found desirable that would function to support the surface and yet allow very quick distribution and cooling by the cryogenic fluid, while being insulated from the remainder of an associated plate. A disc that places or distributes a cryogenic fluid beneath the entire surface very rapidly, especially from a centrally located chamber aligned with a center of the specimen, while also effectively drawing away evaporated gases was deemed to be an important improvement in the apparatus. It was especially desirable for the cryogenic fluid to first be distributed near and beneath the center of the surface to be cooled and then allowed to flow outward therefrom in a generally symmetrical or uniform pattern.

Furthermore, in order to reduce the time required for cooling a sample, it was desirable to convey the cryogenic fluid so as to be closely adjacent to the surface to be cooled and to likewise provide structure to allow gases formed as the cryogenic liquids evaporate and change into a gaseous phase to be rapidly conveyed away. In order to improve the function of propelling the cryogenic fluid so the liquid is quickly conveyed to the area associated with the surfaces for cooling and so the evaporated gases are quickly conveyed away from this region, the concept was devised of both drawing the cryogenic fluid through the system by use of a vacuum and returning the evaporated gases into the cryogenic tank for pressurizing the cryogenic tank to likewise drive the fluid due to pressurization. That is the cryogenic fluid is to be both pulled and pushed by a single operative pump, preferably a vacuum pump.

In general, the improvements to the apparatus represented by the present invention are designed to substantially improve the efficacy of the apparatus and very rapidly and quickly freeze a tissue specimen for use in medical procedures.

SUMMARY OF THE INVENTION

An apparatus is provided for relatively quickly freezing a tissue specimen, especially a human tissue specimen incorporating a cancerous tumor or other non desirable isolated growth surrounded by skin or the like that is not part of the growth. The apparatus utilizes a cryogenic fluid for very rapidly freezing the tissue specimen to allow slicing of layers from the specimen by use of a microtome or the like. While it is foreseen that other cryogenic fluids could be utilized within the scope of the invention, the preferred cryogenic fluid is liquid nitrogen.

The general purpose of the apparatus according to the present invention is to very rapidly freeze a tissue specimen, while substantially reducing the amount of time necessary to prepare and freeze the specimen while providing a high quality processed specimen. The apparatus includes a base supporting a pair of plates or platforms. One of the plates is a rotatable plate and the other is referred to as a linear plate, as it moves in only a linear direction versus the angular direction of the rotatable plate. Although it is foreseen that normally the rotational plate and the linear plate will be two separate plates, it would be possible to incorporate a structure that would move a first plate with an angular motion and thereafter with a linear motion and have a second plate that would be generally stationary. In the embodiment shown herein the two operations are separated such that a rotational plate moves angularly and a linear plate moves linearly.

Positioned on each of the rotational and linear plates are a plurality of discs having surfaces for engaging tissue specimen to be frozen. In the present embodiment the surfaces of the disc on the rotational platform are the receiving surfaces and the surfaces on the linear platform are covering surfaces, but it is foreseen that this could be reversed.

The rotational platform is connected to the base structure by a rotary column. The column allows the rotating platform to rotate about an axis and move from a specimen receiving position to a covering position where it is positioned over the linear platform in a manner such that the discs of each platform are positioned opposite corresponding discs and in facing relationship to one another.

The column includes a conduit manifold that allows flow of cryogenic fluid to the disc and a return of evaporated gas from the disc to a cryogenic fluid tank. The column also includes a cryogenic rotary hinge or junction constructed of interconnected quartz tubes which allow rotation relative to one another at cryogenic temperatures and which provide support for the cryogenic tubing in the column.

Each of the discs are chambered in such a manner as to enhance heat transfer between the cryogenic fluid and the surface of the disc and then subsequently the tissue specimen. That is, each disc includes a centrally located chamber which is centered along an axis that passes through the center of a respective surface and approximately through the center of a specimen placed on the surface.

In particular, each of the discs include a nipple which connects to a cryogenic fluid supply and that opens into a first or distribution chamber that is located closely adjacent the surface of the disc and separated therefrom by a relatively thin wall. The distribution chamber has flow connected thereto a series of radially extending bores which allow flow of the cryogenic fluid radially outward from the center of the disc toward the exterior thereof.

A second or collection chamber is located on the opposite side of the first chamber from the surface. The second chamber also connects with a series of radially constructed bores which are preferably somewhat larger than those associated with the first chamber and which are designed to collect evaporated gas that has been evaporated in the first chamber and in the bores associated with the first chamber. The second chamber and the bores associated therewith are connected with the first chamber and the bores associated therewith through channels that are on the radial outer portion of the disc. The collected gas in the second chamber flow connects with a return tube through a second nipple.

An insulating sleeve surrounds each disc to help insulate each disc from the platform supporting the disc. The discs provide for very rapid conversion of liquid nitrogen or other cryogenic fluid from a liquid phase to the gaseous phase with a consequent transfer of heat from the disc to be fluid to provide the enthalpy necessary for the phase conversion. This transfer of heat to the cryogenic fluid rapidly cools the discs, especially the surface located adjacent the distribution chamber, and subsequently rapidly cools the tissue specimen supported by the surface thereof.

The cryogenic fluid system provides improved flow of cryogenic fluid to and through the disc compared to the prior art, so as to very rapidly cool the disc. In particular, a vacuum pump is connected to the tubing associated with the discharge of evaporated gas from each disc. In operation the vacuum pump associated with the cryogenic fluid system draws a vacuum on the evaporated gas tubing exiting each of the discs. A cryogenic fluid source such as a tank of liquid nitrogen is flow connected with the cryogenic fluid supply or delivery tubes entering each disc. The vacuum pump in this manner operably draws the cryogenic liquid into the disc where the liquid evaporates into a gas due to heat from the disc and specimen supported thereby and the vacuum pump draws the evaporated gas from the disc. The evaporated gas is then conveyed back to the top of the cryogenic liquid tank so as to increase the pressure therein and in this manner help propel the liquid through the fluid delivery line. Preferably the supply tubes are sized to encourage flow of the cryogenic fluid therethrough.

When a tissue specimen is placed on a receiving surface for freezing, it is initially required that the specimen be flattened against the receiving surface. Normally the tissue sample is placed so that a curved surface initially engages the receiving surface. Because the curved surface is not initially flat, the sample must be flattened. This is accomplished with the present apparatus by placing a layer of flexible plastic material, such as saran film, over the tissue specimen.

At least a pair of channels are formed in the plates supporting the receiving surface and associated discs in closely spaced circumferential relationship to a respective surface. The channels are each connected to a vacuum pump. In operation the saran film is placed over the tissue sample and the vacuum pump is initiated so as to draw the saran film layer tight against surface of the plate and to draw gases from about the tissue specimen. This snugs the specimen against the receiving surface and, in particular, pushes the specimen flat against the surface. Manual manipulation on top of the film may also be required to ensure that the specimen is flat against the receiving surface.

Once the specimen is placed on the receiving surface and flattened, additional specimens may be placed on similar receiving surfaces or the single specimen may be frozen in accordance with the present invention. Often where a relatively large tumor, especially an internally located tumor, is to be studied, the tumor may be divided into independent sections, four for example, and each section is located on a separate receiving disc. The plastic material layer is positioned over the specimen and the specimen is flattened in accordance with the description above. Once this is accomplished, the rotating platform is swung about its axis so that it is in covering relationship to the linear platform. The linear platform then moves linear toward the rotational platform without substantial lateral movement in such a manner as to engage, but not roll the specimen from side to side.

Thereafter, the vacuum pump associated with the cryogenic fluid system is operated to draw cryogenic fluid into the disc associated with the specimen and to evaporate the cryogenic fluid therein due to heat transfer from the disc and subsequently from the specimen. This causes a very rapid cooling of the specimen which freezes within a relatively very short time. The vacuum pump discharges the gases therefrom into the top of the cryogenic fluid storage tank so as to pressurize the tank and thereby further motivate flow of cryogenic fluid therefrom. Preferably, tubing conveying the gaseous portion of the cryogenic fluid also includes a holding tank upstream of the vacuum pump which is positioned in such a manner as to have a flow control valve located between the tank and an associated disc. The tank allows the vacuum compressor to evacuate the interior chamber thereof in anticipation of the control valve being opened to draw gas from the disc.

OBJECTS AND ADVANTAGES OF THE INVENTION

Therefore the objects of the present invention are: to provide an apparatus for relatively very rapidly freezing tissue samples; to provide such an apparatus that includes a pair of platforms that allow a tissue sample to be placed on a receiving surface on one of the platforms and the specimen to also engage an opposed surface on the second platform that are rotated relative to each other so that the specimen is sandwiched therebetween; to provide such an apparatus wherein cryogenic fluid is utilized to rapidly cool discs associated with the receiving and opposite surfaces so as to very rapidly freeze tissue specimen therebetween; to provide such an apparatus wherein the rotating platform is connected to a remainder of the apparatus by a pivoting or rotating column having cryogenic fluid lines passing therethrough; to provide such an apparatus wherein the pivoting column includes a rotating pivot junction constructed of coaxial and joined quartz tubing in surrounding relationship to conduit for a cryogenic fluid; to provide such an apparatus having a linear platform which moves in a linear direction toward the rotating platform once the rotating platform has been positioned over the linear platform; to provide such an apparatus having a latch mechanism for automatically triggering the linear platform to move toward the rotating platform once the rotating platform is in position above the linear platform; to provide such an apparatus including cryogenic evaporation discs associated with both the specimen receiving and covering surfaces for rapidly evaporating cryogenic fluid, thereby cooling the discs and associated specimen; to provide such an apparatus wherein the discs include a central chamber for receiving and distributing cryogenic fluid connected to a series of radially extending bores for conveying fluid radially in close proximity to the surface with a similar structure for collecting evaporated gases; to provide such an apparatus having a series of channels circumferentially surrounding each of the discs and joined with a vacuum drawing system, such that, when a plastic layer is operably placed over each of the specimens in covering relationship to the surface and each of the channels, then a vacuum is drawn beneath the layer through the channels so as to urge the specimen tight against the surface and flatten the side of the specimen facing the surface; to provide a method for using such an apparatus wherein a tissue specimen is cooled very rapidly and such that a relatively short period of time is required to prepare and freeze the specimen; to provide such an apparatus which is relatively easy to use, inexpensive to produce and particularly well suited for the intended usage thereof. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 7 is a fragmentary cross sectional view of the apparatus, taken along line 7—7 of FIG. 4, showing the apparatus in the tissue freezing configuration thereof.

FIG. 8 is a fragmentary cross sectional view of the apparatus taken along the same cut line as FIG. 7 and illustrating the apparatus in the tissue receiving configuration thereof.

FIG. 9 is a fragmentary cross sectional view of the apparatus taken along line 9—9 of FIG. 8.

FIG. 10 is a fragmentary and perspective view on an enlarged scale of the apparatus, showing a trigger and latch mechanism thereof.

FIG. 11 is a substantially enlarged, fragmentary and cross sectional view of the apparatus, taken along line 11—11 of FIG. 3.

FIG. 12 is an enlarged, fragmentary and cross sectional view of the apparatus especially showing a freezing disc, taken along line 12—12 of FIG. 1.

FIG. 13 is an enlarged and fragmentary view of one of the freezing discs, with portions broken away to show detail thereof.

FIG. 14 is a fragmentary and cross sectional view of a rotary junction operationally located in a central portion of a support column shown in FIG. 11 subsequent to assembly of the junction and before placement in the remainder of the associated support column.

FIG. 15 is an exploded perspective view of the rotary junction illustrated in FIG. 14 prior to assembly thereof.

DETAILED DESCRIPTION OF THE INVENTION

Figure 1:
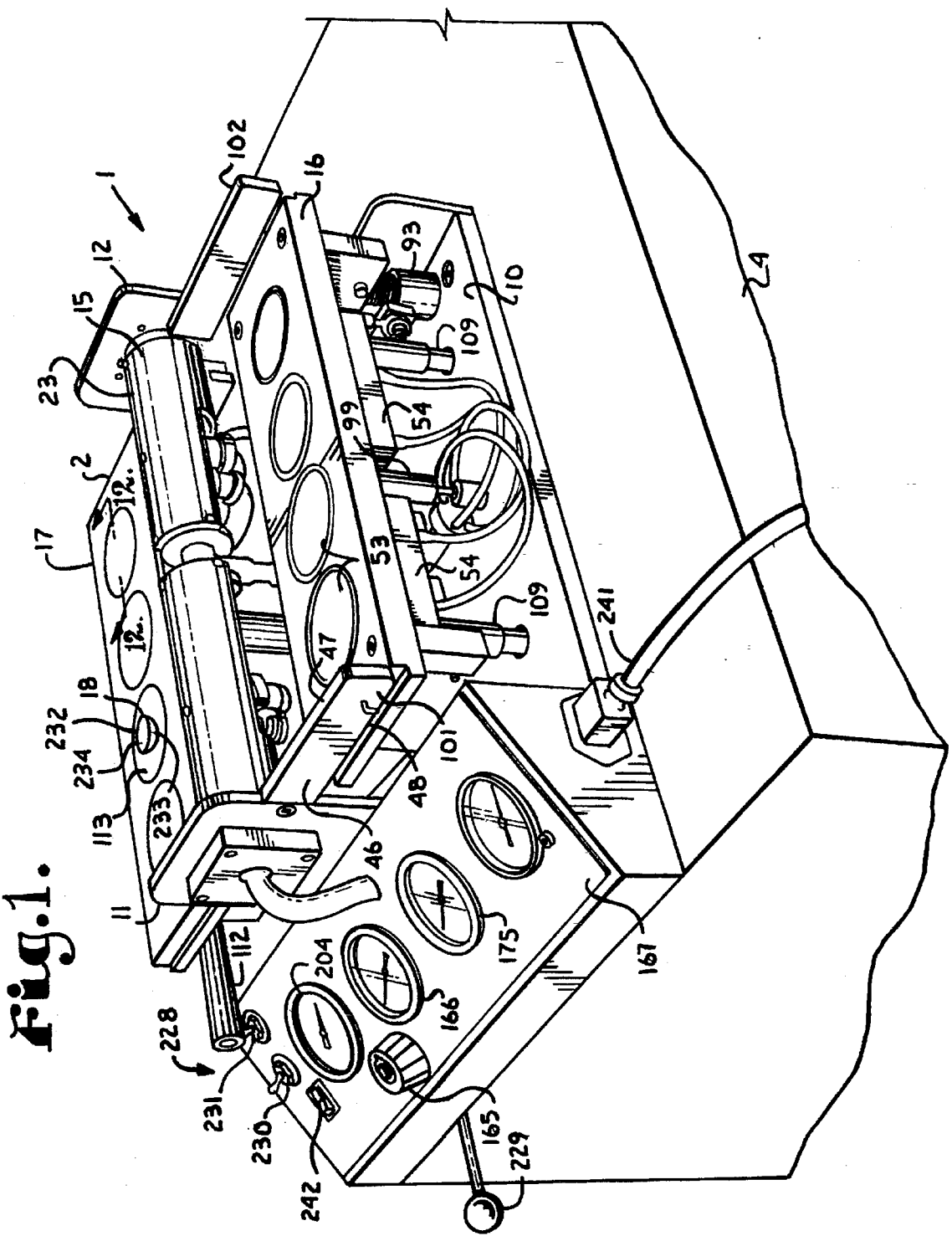
FIG. 1 is a perspective view of a tissue freezing apparatus in accordance with the present invention, including a fragmentary cabinet for enclosing a liquid nitrogen storage tank and flow system and illustrating the apparatus in a tissue receiving configuration thereof.
Figure 2:
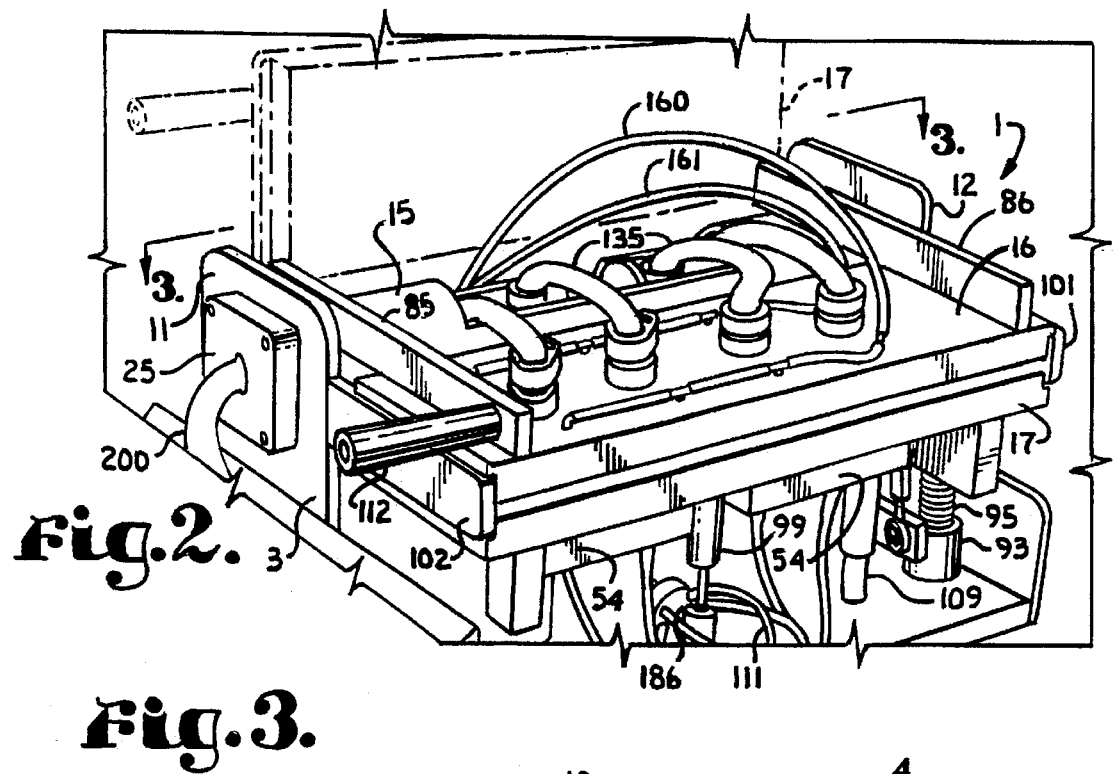
FIG. 2 is a fragmentary and perspective view of the apparatus, illustrating the apparatus in a tissue freezing configuration thereof in solid lines and showing a transition position between the tissue receiving configuration and the tissue freezing configuration for a rotating platform in phantom lines.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents a tissue specimen freezing apparatus in accordance with the present invention. The apparatus 1 includes a platform mechanism 3 supported by a cabinet 4 containing a portion of a fluid transfer system 5 which is generally schematically represented in FIG. 6.

The platform mechanism 3 includes a base 10 that is positioned on and supported by the cabinet 4. Extending upward from the front and rear ends of the base 10 are front and rear support panels 11 and 12 respectively. The support panels 11 and 12 support therebetween in spaced relationship relative to the base 10 a central column 15, a linear motion platform 16 and a rotary or rotatable motion platform 17. The function of the platforms 16 and 17 is to receive a specimen 18, see FIG. 5, therebetween and to very rapidly freeze the specimen 18.

The column 15 helps support the rotatable platform 17 and effectively supports a piping arrangement 20 for conveying liquid cryogenic fluid, especially nitrogen, to the rotatable platform 17, and conveying gaseous nitrogen away from the rotatable platform 17, as will be described later and is shown schematically in FIG. 6. While the present system is especially designed for use in conjunction with nitrogen because it is generally inert and non combustible, the apparatus 1 may be used in conjunction with other cryogenic fluids.

Because the cryogenic fluids that provide the very rapid freezing of a specimen 18 are at relatively very low temperatures, normally at least several hundred degrees below zero Fahrenheit, the column 15 is susceptible to substantial stress due to very rapid change in temperature that act to lockup the rotational movement and is also susceptible to freezing that actually forms a frozen bond between parts that would prevent rotation of the rotatable platform 17. At least a portion of the structure of the column 15 described below is constructed to be able to withstand the sudden and rapid changes in temperature, while still allowing free rotation of the rotatable platform 17.

Figure 4:
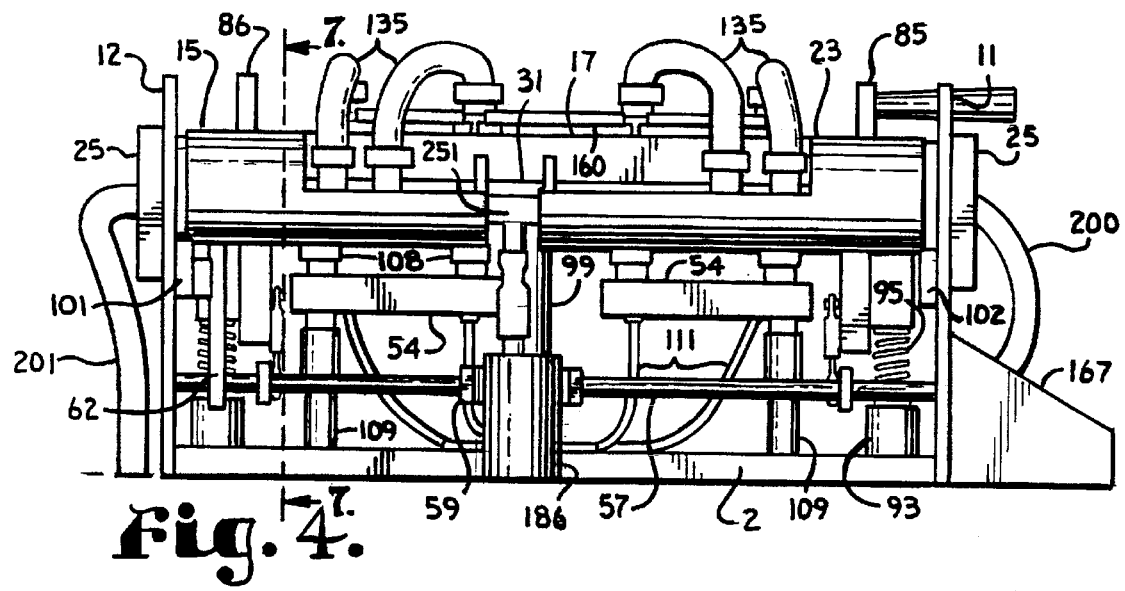
FIG. 4 is a fragmentary first side elevational view of the apparatus, showing the apparatus in the tissue freezing configuration thereof.

The left hand side of the column 15, as is seen in FIG. 4, is illustrated in greater detail in FIG. 10. The right hand side of the column 15 is in general a mirror image of the left hand side shown with certain dimensional differences.

The column 15 includes a partial tubular structure 23, a pair of end plugs 24, a pair of mounting plates 25 and a pair of central supports 26.

The tubular structure 23 is preferably constructed of a metallic or other relatively non flexible and stable material. The tubular structure 23 has an axially extending cut out 28 that extends along the central approximately three fourths of the tubular structure 23 and which provides ready access to the piping arrangement 20 therein. A small and more extensive cutout 29 with yet a further circular cutout 30 is near the center of the tubular structure 23 and is positioned to allow a portion of the piping arrangement 20 to extend therethrough and remain in fixed relationship to the tubular structure 23 as the latter rotates. A bridge 31 joins opposite sides of the tubular structure 23 at the cutout 29.

The end plugs 24 are generally circular and are sized in shape to fit into the end of the tubular structure 23 so as to support the latter. The end plugs 24 are preferably constructed of the same material as the tubular structure 23 and a suitable material construction has been found to be aluminum. The end plugs 24 have a recess on the tubular structure side thereof which receives and securely holds an end 34 of the tubular structure 23.

Each end plug 24 is respectively mounted in one of the mounting plates 25. In particular, each mounting plate 25 is secured to a respective support panel 11 and 12 at apertures 36 in the latter. Each of the mounting plates 25 has a centrally positioned circular recess 37 which is sized and shaped to slideably receive a circular projection 39 extending from a respective end plug 24. The position and alignment of the circular recess 37, of the mounting plate 25, the circular projections of the end plugs 24 and the overall axis of the tubular structure 23 is such as to allow rotation of the tubular structure 23 about a central axis thereof identified by the reference letter A in FIG. 10. Preferably, the mounting plates 25 are constructed of a material that allows relatively free rotation of the end plugs 24 therein and has been found that tetrafluoroethylene functions well for this purpose and the tubular structure 23 is preferably constructed of aluminum. That is, the end plugs 24 with the tubular structure 23 attached rotate relatively freely in the mounting plates 25 about the axis A.

The central supports 26 are generally circular in shape and are fixed to the inside of the tubular structure 23 by screw fasteners or the like (not shown). Each of the central supports 26 has a centrally located bore 42 which is aligned with the tubular structure axis A and which is sized and shaped to receive a portion of the piping arrangement 20 therethrough. Each of the central supports 26 has a laterally extending flange 43 around the bore 42.

Figure 5:
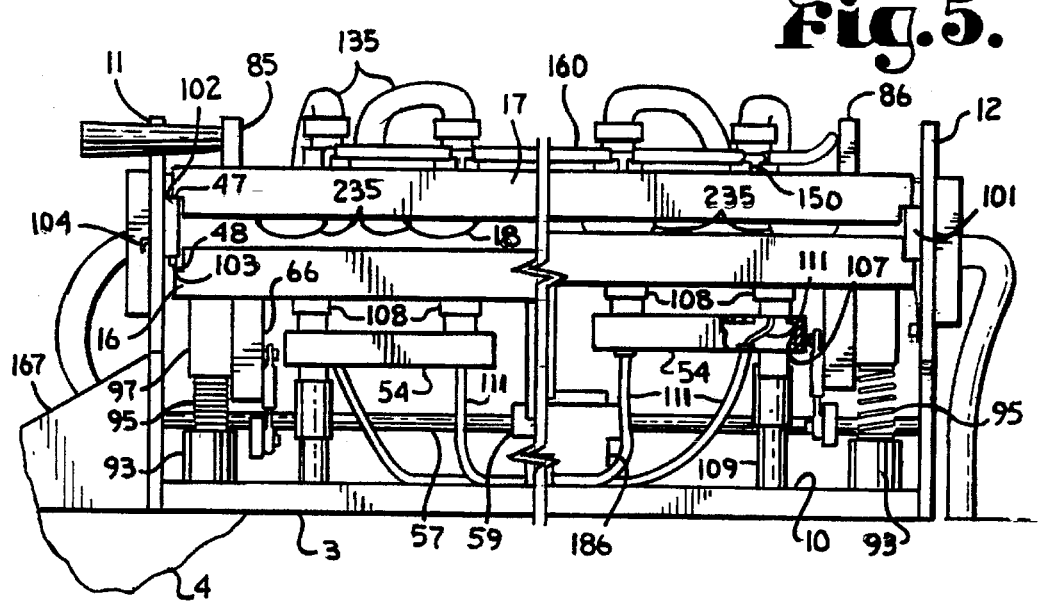
FIG. 5 is a fragmentary second side elevational view of the apparatus, showing the apparatus on the right side of the view in the tissue freezing configuration thereof and on the left side in a second intermediate and covering configuration thereof.

The linear platform 16 is best illustrated in FIGS. 1, 2, 5, and 7 through 9. The linear platform 16 moves with a non angular and non pivotal motion during operation of the apparatus 1. This movement is illustrated in FIG. 5 wherein the linear platform 16 moves between the positions shown in the left hand side of the figure and the right hand side of the figure. While this movement is relatively small, it is important. In particular, the rotatable platform 17 swings almost 180° about the apparatus 1 when moving from a tissue receiving position such as is shown in FIG. 1 to a tissue freezing position such as is shown in the right hand side of FIG. 5. This movement is fairly substantial.

The specimen 18 is extremely susceptible to being mispositioned if there is any side to side movement between the platforms 16 and 17 when engaging the specimen 18. If the platforms 16 and 17 move from side to side when engaged, the specimen has a tendency to turn up on the flattened edge or margin 50 and to create other problems that make the specimen less than suitable for use once frozen. If the rotatable platform 17 is allowed to engage the specimen 18 during rotation of the rotatable platform 17, as will be described below, the specimen 18 has a tendency to be moved somewhat horizontally. Consequently, the rotatable platform 17 moves in an arc as will be described below over the linear platform 16 and is positioned there by a stop device 46 fixedly mounted on the front panel 11. The stop device 46 has an upper engagement surface 47 which engages the rotatable platform 17 at a preselected distance from the linear platform 16 and prior to the linear platform 16 moving toward the rotary platform 17, as is illustrated on the left hand side of page 5. The linear platform 16 then moves upward to engage a lower engagement surface 48 of the stop 46, as is seen in FIG. 5 on the right hand side.

The linear platform 16 is referred to as being linear as its movement is strictly linear, here vertical, movement. That is, the linear platform 16 moves vertically toward the rotatable platform 17 in such a manner as not to inject any angular or horizontal movement therebetween and which generally compresses the specimens 18 rather than exerts any sideways movement thereon. It is foreseen that in accordance with the present invention a first platform could move first with a rotary motion and then with a linear motion while a second platform is relatively stationary or that there could be some sharing of the linear movement.

Associated with the linear platform 16 is a latch and trigger mechanism represented by the reference numeral 51, a biasing mechanism 52, a plurality of cryogenic specimen receiving discs 53 and a pair of plenums 54.

The latch and trigger mechanism 51 is designed to release the linear platform 16, to move slowly upwardly after the rotatable platform 17 has moved into the covering position thereof shown in FIG. 5 wherein the rotatable platform 17 is positioned directly above the linear platform 16. Parts of the latch and trigger mechanism 51 can be seen in FIGS. 7 through 9. The latch and trigger mechanism 51 includes a series of components which are designed to hold the linear platform 16 in a lowered position, as seen on the left hand side of FIG. 5, and then release it to allow the platform 16 to raise to the raised or specimen engaging position seen on the right side in FIG. 5.

The latch and trigger mechanism 51 includes a circular bar 57 which is rotatably within a pair of opposed bearings 58 which are respectively mounted in the front and rear support panels 11 and 12. A central portion of the bar 57 includes a crescent shape section 59 that allows the bar 57 to rotate, even though the rotational axis of the bar 57 passes through other structure which will be described below. Attached to the bar 57 near the left hand side thereof, as is seen in FIG. 4, is a generally vertically aligned lever arm 62. Also attached to the bar 57 are a pair of generally horizontally aligned lever arms 63 near opposite ends thereof. The arms 62 and 63 are fixed to the bar 57 so as to rotate therewith and are aligned at approximately 90° relative to each other.

Extending downward from each side of the linear platform 16 are a pair of structural members 66 which are fixedly attached to the underside of and near opposite ends of the linear platform 16. A pair of freely pivoting bars 68 are connected at opposite ends thereof to a respective structural member 66 and a distal end of one of the horizontal arms 63 by fasteners 69 that allow relatively free rotational movement of the pivoting bar 68 relative to the structural member 66 and horizontal arm 63 to which the bar 68 is attached.

The latch and triggering mechanism 51 also includes a latch 72 for engagement with the distal end of the vertical arm 62. The latch 72 includes an elongate member 74 and a biasing mechanism or spring 75. The elongate member 74 is pivotally attached to a stop 78 by a bolt 79 passing through the left hand side of the elongate member 74, as is seen in FIGS. 7 and 8. The stop 78 is fixedly secured to the rear support panel 12 and operably supports and positions the rotary platform 17. The elongate member 74 has a lip or shoulder 81 that extends generally vertically along a face 82 thereof that is engageable with the vertical arm 62. The spring 75 biases the elongate member 74 to rotate on the bolt 79 toward the vertical arm 62 which is allowed to pivot on an axis that passes through the bar 57. When the arm 62 and linear platform 16 are in a specimen receiving position, as is shown in FIG. 8, the lip 81 engages and secures the vertical arm 62 thereagainst until released. When the arm 62 and linear platform 16 are in a specimen engaging position, as seen in FIG. 7 and the right side of FIG. 5, the arm 62 is not received against the lip 81 and is free to rotate to the left, in the view seen in FIG. 7.

The rotatable platform 17 includes a pair of arms 85 and 86 which are securely attached to the column tubular structure 23 so as to rotate therewith. The arms 85 and 86 support and allow rotation of the rotatable platform 17 which will be described in greater detail below. Extending outwardly from the arm 85 is an arm following pin or projection 88 which extends toward the elongate member 74 and which during rotation of the tubular structure 23 engages the vertical arm 62 and urges the distal end of the arm 62 to the right as seen in FIG. 8. In particular, when the pin 88 is engaged with the vertical arm 62, as is shown in FIG. 8, the arm 62 is pushed to the right, as the structure 23 rotates to place the rotating platform 17 in the open or tissue receiving position seen in FIG. 1, and the lip 81 is allowed to ride along and bias the side of the arm 62 so that the arm 62 is positioned alongside the lip 81 at which time the spring 75 urges the arm 62 to seat on the lip 81 so as to secure the arm 62 in the position shown in FIG. 8. In this configuration, the arm 62 is locked in such a position as to hold the bar 57 and consequently the horizontal arms 63 in a locked position which in turn holds the pivoting bars 68 downward and the linear platform 16 in the downward position seen in FIG. 8 wherein the linear platform 16 does not engage the specimen 18.

Mounted on the tubular structure 23 is a second pin or projection 90 which is located so as to extend radially outward therefrom. When the rotatable platform 17 is in the specimen receiving position shown in FIG. 8, the pin 90 extends upwardly and is free of engagement with other structure. However, when the rotatable platform 17 is rotated to a position where it covers the linear platform 16, such as is shown in FIG. 7 and in the left hand side of FIG. 5, the pin 90 engages a camming surface 91 of the elongate member 74 which urges the elongate member 74 away from the vertical arm 62 and which thereby disengages the vertical arm 62 from the elongate member lip 81. Once the arm 62 is free of the lip 81, the biasing mechanism 52 then urges rotation of the entire system including the vertical arm 62, the bar 57, and the horizontal arms. This in effect allows the linear platform 16 to raise.

In particular, the linear platform 16 is also supported by the biasing mechanism 52 which is best seen in FIG. 9. The biasing mechanism 52 includes a pair of anchors 93 positioned near opposite ends and below the platform 16. The anchors 93 are fixedly attached to the apparatus base 10. Located in and extending upwardly from each of the bases 93 is an elongate cylindrical post 94. Secured about each post 94 on top of each base 93 is a compression spring 95.

Each post 94 is received in a bore 96 located in opposite ends of the linear platform 16. The bores 96 are of somewhat greater diameter then the post 94 to allow free movement therebetween. Also freely surrounding each post 94 is a sensor 97 to determine the position of the linear platform 16 with a bore 98 extending therethrough.

In this manner, the spring 95 continuously biases the linear platform 16 upward, while the latch and triggering mechanism 51 generally controls the positioning of the linear platform 16 in lower specimen non engaging or upper specimen engaging configurations. In particular, when the vertical arm 62 engages and is held by the elongate member lip 81, the linear platform 16 is locked in a lowered position and cannot move upwardly. When the pin 90 engages the camming surface 91 on the elongate member 74 so as to release the vertical arm 62 from the elongate member lip 81, then the linear platform 16 is released to move upwardly under the biasing pressure of the springs 95. The speed of the upward movement of the linear platform 16 is controlled by a gas piston 99 which is positioned near the middle of the linear platform 16 and which is fixedly connected to both the apparatus base 10 and the underside of the linear platform 16.

The stop device 46 includes a first stop 101 on the front support panel 11 and a second stop 102 on the rear support panel 12 which operably limit the uppermost vertical extension of the linear platform 16 and the minimum spacing between the rotatable platform 17 and the linear platform 16, as can be seen on the right hand side in FIG. 5. That is, the stops 101 and 102 also act as rests and as limiting stops to the rotatable platform 17, when the platform 17 is in the covering configuration, as is seen in both the left and right side of FIG. 5. An eccentric cam 103 is located on the lower side of the stop 102 and includes a handle 104 which rotatably passes through the front support panel 11. The cam 103 allows a user of the apparatus 1 to selectively adjust the maximum vertical extension of the linear platform 16 so that the spacing of platforms 16 and 17 while engaging a specimen 18 during freezing, as is shown on the right hand side of FIG. 5, can be adjusted for large or small specimens as necessary.

Mounted within and supported by the linear platform 16 are four of the cryogenic discs 53. Each of the discs 53 is generally evenly spaced from adjacent discs 53 along the upper surface of linear platform 16 so as to face upwardly therefrom. The discs 53 will be discussed in greater detail below.

Mounted on the underside of the linear platform 16 are the plenums 54. Each of the plenums 54 include an inner chamber 107. Each plenum inner chamber 107 is flow connected to a pair of tubes 108 which are in turn each connected to a respective cryogenic disc 53. Each plenum 54 is also flow connected to a discharge tube 109 which passes through the base 10 and into the cabinet 4. A pair of liquid nitrogen tubes 111 each sealably pass through the lower wall of each of the plenums 54 and each pass through a respective tube 108 to be joined with a respective cryogenic disc 53, as will be discussed below.

The rotatable platform 17 is supported by the arms 85 and 86, as has been described above. Attached to and extending perpendicularly from the arm 85 is an operating handle 112. The rotatable platform 17 is rotatable with the tubular structure 23 such that the rotatable platform 17 can rotate approximately 180° from a tissue receiving position, as seen in FIG. 1, into a covering position above the linear platform 16, as is illustrated in FIG. 5. The rotatable platform 17 has located therein four cryogenic specimen receiving discs 113. Each of the discs 113 faces upwardly when the rotatable platform 17 is in the open or tissue receiving position thereof, as seen in FIGS. 1 and 8, and faces downwardly when the rotatable platform 17 is in the covering position thereof, as seen in FIG. 5. One of each of the cryogenic discs 113 in the rotatable platform 17 is directly positioned above and in facing relationship to a respective one of the cryogenic discs 53 in the linear platform 16, when the rotatable platform 17 is in the covering position shown in FIG. 5. The cryogenic discs 53 and 113 are more fully illustrated in FIGS. 12 and 13. As each of the disc 113 and 53 are essentially identical in structure, the description of either applies to the other.

Specifically directing attention to FIG. 12, the disc 113 is cylindrical in outer configuration and includes a generally planar upper tissue engaging surface 115, a cylindrical outer wall 116 and a lower tube receiving wall 117. The terms upper and lower with respect to the description of this paragraph apply to the disc 113 only as the disc 113 is shown in FIG. 12 and it is realized that these surfaces do vary in orientation with rotation of the rotatable platform 17. A nipple 119 having an internal flow passageway 120 is sealably mounted so as to extend through the axial center of the disc wall 117 as is indicated by the axis identified by the reference letter B. A plurality of generally equally angularly spaced bores 123 pass diagonally entirely through the body of the disc 113. Intermediate bores 124 are positioned between the bores 123 such that the bores 124 pass only half way radially from the outside of the outer wall 116 toward the axial center of the disc 113. The bores 124 join with the bores 123 and all of the bores 123 join centrally to form an open interior chamber 125 which in turn flow communicates with the nipple passageway 120. The chamber 125 is axially centered relative to the disc 113 along the axis B and, along with the bores 123 and 124, is positioned in close proximity to the wall 117.

A second set of bores 127 pass entirely through the disc 113 diagonally and join at a cavity 128 that is axially centered relative to the disc 113 along the axis B. A circumferential groove 129 is located so as to entirely circle the outer wall 116 and so as to flow communicate between the bores 123, 124 and 127.

A threaded bore 132 is located between the chamber 125 and the cavity 128 in a central structural region 131. Threadably received in the bore 132 is a nipple 133 which effectively prevents fluid flow through the bore 132 unless it passes through the nipple 133. In the illustrated embodiment, the bores 123 and 124 have diameters which are approximately three times as great as the diameter of the bores 127.

Received on each of the nipples 119 is a fluid return tube 135 which operably flow connects with the bores 123 and 124 through the nipple passageway 120 and chamber 125. Attached to the nipple 133 is a cryogenic liquid tube 136 which flow communicates through the nipple 133 with the cavity 128 and thus with the smaller bores 127. Preferably, each of the discs 53 and 113 are constructed of a highly heat conductive metal such as aluminum. A non conductive sleeve 138 is positioned in surrounding relationship to the outer wall 116 and has a lower flange 139 upon which an associated disc 53 or 113 sits. A recess 140 is located to receive each of the discs 53 and 113 in the linear platform 16 and rotatable platform 17 respectively. The sleeve 138 is preferably constructed of tetrafluoroethylene. Each of the recesses 140 includes a floor 141 opening into a boer 142 that receives the nipple 119 therethrough. Positioned along the lower wall 117 is a heating element 145. Each of the heating elements 145 can be selectively operated to heat the discs 53 and 113 after usage to warm them for subsequent use. The disc upper surface 115 is preferably crisscrossed with a series of shallow etchings to improve specimen removal after freezing and to improve the removal of air from beneath the specimen 18 during the application of a vacuum thereto as will be further described below.

As is seen in FIG. 12, each of the discs 113 in the rotatable platform 117 are surrounded by a plurality of vacuum channels. In particular, there is a first circumferential groove or channel 148 which opens into the recess 140. The channel 148 is flow connected to a bore 149 which is in turn flow connected to a vacuum tube 150. Radially spaced outward from the first channel 148 is a pair of spaced second and third channels 151 and 152. The channels 151 and 152 both flow connect with a bore 155 which in turn connects with a vacuum tube 156.

Figure 3:
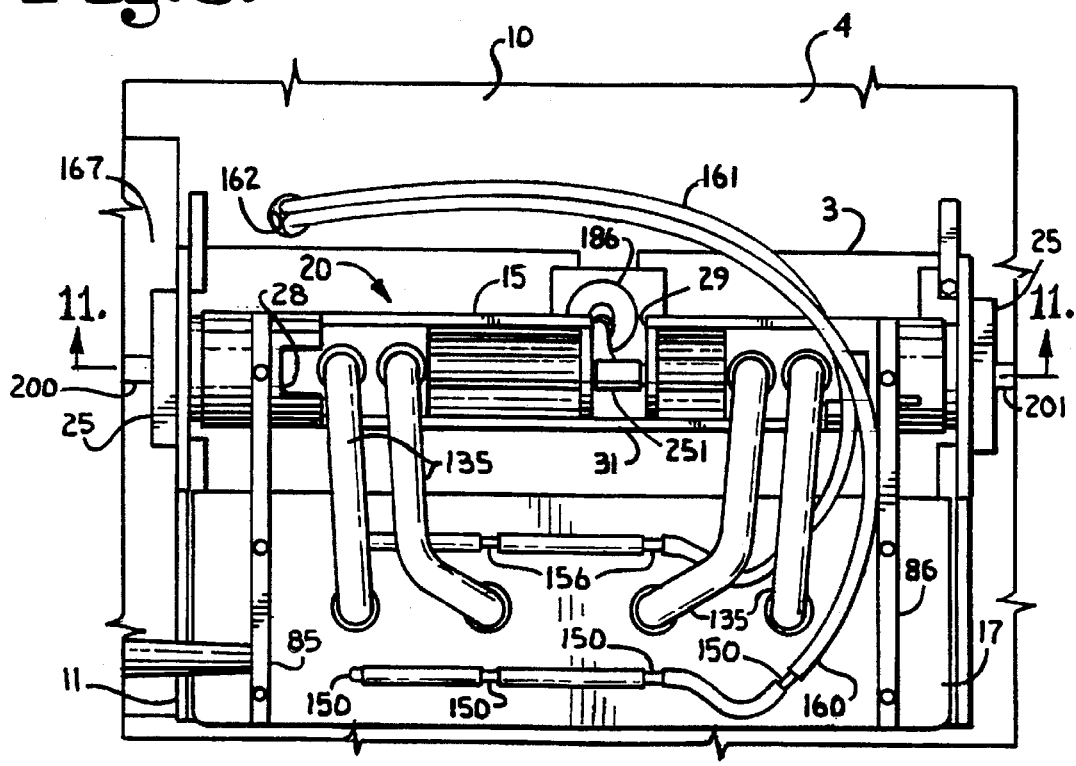
FIG. 3 is a fragmentary top plan view of the apparatus with the apparatus in the tissue freezing configuration thereof.
Figure 6:
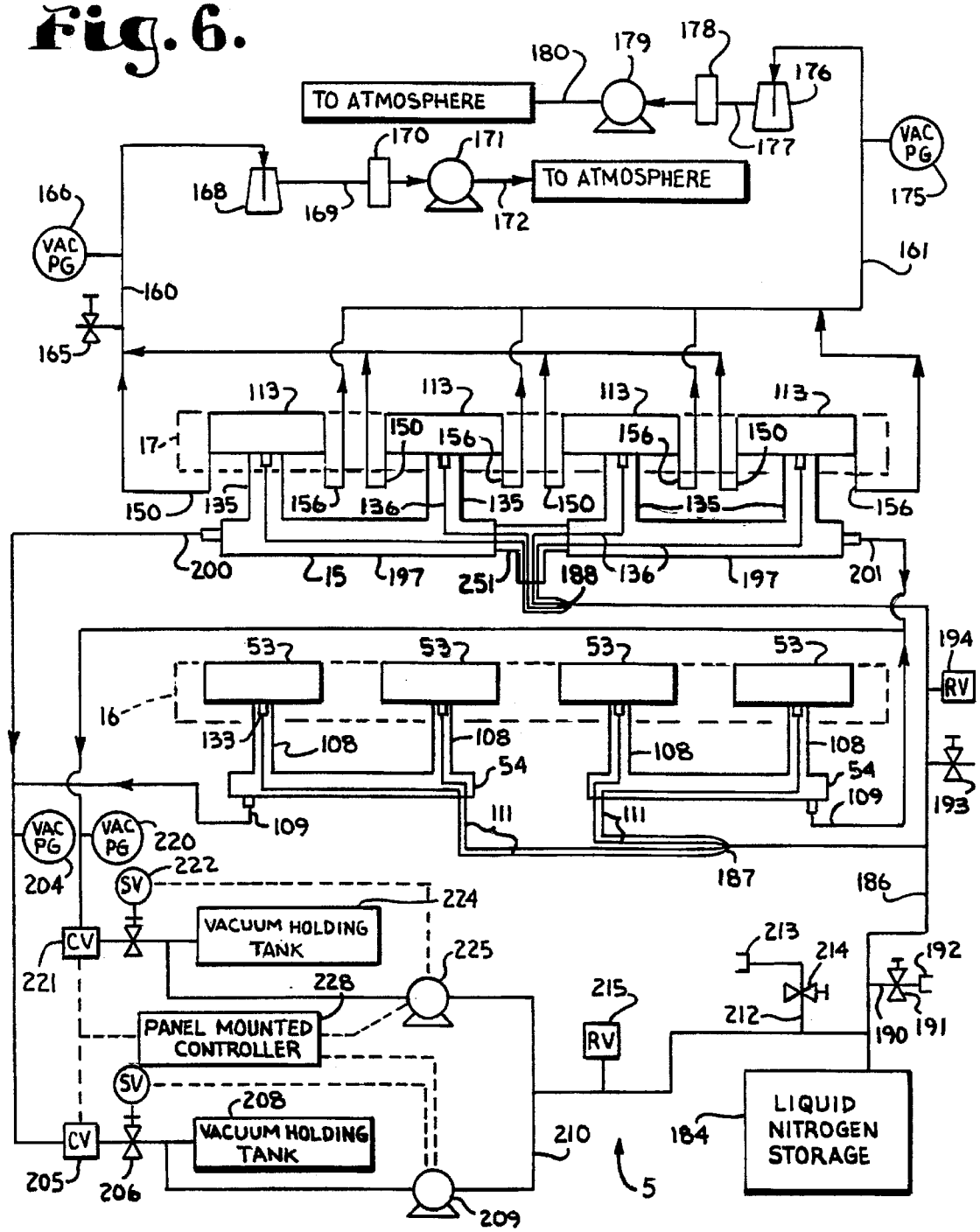
FIG. 6 is a schematic flow diagram of a fluid flow system of throughout the apparatus during operation thereof.

With reference to FIG. 3 and to the schematic diagram shown in FIG. 6, each of the vacuum tubes 150 are joined into a common conduit 160 and each of the vacuum tubes 156 are joined into a common conduit 161. The conduits 160 and 161 pass through the base 10 into the cabinet 4 at an aperture 162. Flow connected with the conduit 160 is a valve 165 and a pressure gage 166 which are both operably located on a control panel 167. The conduit 160 flow opens into a clear glass catch basin 168 for liquid which thereafter flow connects with a conduit 169 that passes through a biological filter 170 into a vacuum pump 171. The vacuum pump 171 discharges through a conduit 172 to the atmosphere. The valve 165 allows a user to selectively release the vacuum in the conduit 160.

The conduit 161 also is flow connected to a vacuum pressure gage 175 which is operably located on the control panel 167. The conduit 161 likewise opens into a clear glass catch basin 176 for liquid which in turn discharges into a conduit 177 that passes through a biological filter 178 which then flow connects with a vacuum pump 179. The vacuum pump 179 discharges through a conduit 180 to the atmosphere.

The fluid transfer system 5 is generally represented by the schematic diagram in FIG. 6 and has certain components which have been described before. Attention is also directed to FIGS. 11 and 12 in the description of the overall system 5.

With specific reference to FIG. 6, cryogenic fluid such as liquid nitrogen at or below −195.5° centigrade is stored in a jacketed cryogenic tank 184. The liquid cryogenic fluid tubes 111 and 136 are positioned to extend into the storage tank 184 to near the bottom thereof. Preferably the tubes 111 and 136 have an inside diameter that is in the range of 0.051 to 0.074 inches. Within such diameters, the liquid nitrogen in the tubes 111 and 136 will autoperfuse to improve the efficacy of the transfer of the liquid nitrogen, as is further described below.

The tubes 111 and 136 are enclosed within a common carrier tube 186 until they approach the platforms 16 and 17 at which time they separate as is schematically indicated at reference points 187 and 188. The tube 186 also has a liquid fill line 187 connected therewith which is connected to a hose coupling 192 for use in operably filling the tank 184. A manual bleed valve 193 and a relief valve 194 are also flow connected with the tube 186.

The tubes 111 and 136 preferably provide for the flow of liquid nitrogen to the discs 53 and 113 respectively to be discharged into the upper cavities 128 thereof. As has been previously mentioned, the discharge from each of the discs 53 and 113 enters the tubes 108 and 135 respectively. This discharge is normally gaseous, but may include some liquid. The discharge from the tubes 135 is collected in receivers 197 having internal chambers 198, as is seen in FIG. 11. A pair of tubes 135 flow into each receiver 197. The receivers 197 flow communicate with the fluid from the tubes 135 and discharge into tubes 199 which in turn flow connect with a front collection tube 200 and a rear collection tube 201.

With reference to FIG. 6, the tube 201 is flow connected with a vacuum pressure gage 204 which is mounted on the panel 167. The flow through the tube 200 is controlled by a control valve 205 and a solenoid valve 206. The tube 200 is flow connected to a holding tank 208 and to a vacuum pump 209. The vacuum pump 209 discharges into a conduit 210 which in turn preferably flow communicates with the gaseous level in the liquid nitrogen tank 184. The conduit 210 includes a flow line 212 which is joined to a hose connector 213 through a valve 214 to allow access to both the discharge and gas phase of the tank 184. The conduit 210 is also flow connected to a relief valve 215.

The collection conduit 201 is flow connected to a vacuum pressure gage 220. The flow through the conduit 201 is controlled by a control valve 221 and a solenoid valve 222. The conduit 201 further communicates with a holding tank 224 and a vacuum pump 225. Discharge from the vacuum pump 225 is discharged into the conduit 210.

The control valves 205 and 221 are interconnected with a controller 228 including a hand activator 229 which is mounted at the control panel 167. The controller 228 includes a first panel mounted switch 230 for pump 209 and valve 206 and a second panel mounted switch 231 for pump 225 and valve 222 allows a user of the apparatus 1 to turn on either or both of the pumps 209 and 225 while placing or having a respective control valve 205 and 221 in an open position thereof. A power cord 241 operably connects to an electrical outlet to supply power to the pumps 209 and 225 as well as the other electrically operated systems through the controller 228. The valves 206 and 222 are electrically connected to the pumps 209 and 225 respectively to block flow through the conduits 200 and 201 respectively until such time as the operator initiates operation of one or both of the vacuum pumps 209 and 225. Each of the pumps 209 and 225 is associated with two groupings of discs 53 and 113.

The support column 15 includes a rotatable cryogenic junction generally designated by the reference numeral 251. The junction 251 is important to the operation of the apparatus 1 in that it allows for rotation of the column 15 at a pivotal connection whereat portions of the column 15 are cooled substantially due to flow of cryogenic fluids therethrough and wherein the temperature is subject to substantial changes between such cooling and thereafter being warmed to room temperature. Many materials of construction will not function under such a wide range of temperatures, especially at cryogenic temperatures, as such a junction constructed with other types of materials may literally freeze up (one part adhere to another) due to the cold or may lock in position due to elongation or shortening of certain pieces of the juncture due to extremes in cold or variations in temperature. The junction 251 is shown on the right hand side of FIG. 11 with cryogenic tubing 136 passing therethrough and positioned within the column 15. The juncture 251 is shown assembled, but without the cryogenic tubing in FIG. 14 and in an exploded view before assembly in FIG. 15.

The juncture 251 includes a first lateral quartz tube 253 and a second lateral quartz tube 254 slideably received within a central quartz tube 255. The central quartz tube 255 has a centrally located opening 258 that extends circularly through the wall thereof. A tubular tail piece 259 has a shoulder 260 at one end thereof that is securely mounted within the central opening 258 of the central tube 255 when assembled, as is shown in FIG. 14. The lateral tubes 253 and 254 slideably and rotatably move within opposite sides of the central tube 255 even at cryogenic temperatures to allow rotation of the column 15 relative to the tail piece tube 259, the cryogenic supply tubes 136 that pass therethrough and the other related structure.

A T-shaped sleeve 263 constructed of plastic or other material is positioned in surrounding relationship to the quartz tubing 253, 254, 255 and 259 and includes a cross bore 269 which is larger in diameter than the diameter of the lateral tubes 253 and 254 so as to not impede rotational movement thereof. The T-shaped sleeve 263 helps support and insulate the quartz tubing. A second insulating sleeve 254 is mounted around the upper portion of the T-shaped sleeve 263. The sleeve 264 includes a central aperture 265 that surrounds the lower portion of the T-shaped sleeve 263 with a slit 266 on either side thereof that allows for placement of the cover sleeve 264 over the T-shaped sleeve 263. The final assembly of the juncture 251 is shown in FIG. 14. The quartz tubes 253 and 254 rotate about the axis A and freely within the central tube 255 and relative to the remainder of the junction 251. The tubes 253 and 254 may slide axially along tube 255 and the axis A due to elongation or shrinkage during heating or cooling of the apparatus 1. It is believed in accordance with the present invention that the quartz structure is less likely to encounter problems due to temperature change as compared to many conventional materials of construction.

In use, an operator of the apparatus 1 takes a tissue specimen 18 and places it on one of the rotatable platform discs 113 so that the specimen becomes a disc received tissue specimen 232, such is illustrated on the second disc in FIG. 1. Initially, the tissue specimen 232 typically has a very curved lower surface 233 and a generally planar or at least comparatively planar upper surface 234. The upper surface 234 often is an outer layer from which tissue to be studied has been removed (such as skin surface) and, therefore, is generally, but not always, relatively flat in comparison to the underside 233. In particular, the underside usually represents a "scooped out" or excised portion which hopefully includes all of a tumor or the like. In excising the tissue specimen 232, the underside is usually somewhat parabolically or spherically curved. Unfortunately, it is of particular interest to a person studying the tissue specimen 232 to have the underside 233 be flat.

Consequently, the tissue specimen 232 is covered with a generally clear pliable polymeric film such as a saran film 236 shown in FIG. 12. The vacuum pumps 171 and 179 are then simultaneously initiated by a control switch 242 to effectively draw gases from and create a vacuum through conduits 160 and 161 that in turn draw gases from and create a vacuum in the channels 148, 151 and 152 respectively adjacent to the disc 113 (see FIG. 12). By drawing a vacuum in the channels 148, 151 and 152, the saran film is drawn tightly against the disc 113 which draws the tissue specimen 232 snug against the disc surface 115 as is shown in FIG. 12. The previously very curved tissue specimen under surface 233 thus is relatively flattened against the disc surface 115 and the tissue specimen upper surface 234 becomes more curved.

The operator of the apparatus 1 may freeze only a single tissue specimen 232 or may fill all four of the discs 113 with tissue specimen in accordance with previously described method. Each specimen 232 is preferably centered on a respective disc 113 along axis B. Once all the tissue specimens 232 are properly positioned and secured to the discs 113 with film 236, the rotatable platform 17 is rotated from the position seen in FIG. 1 to the position seen in FIG. 5. As the rotatable platform 17 becomes close to the position shown in FIG. 5, the pin 90 engages the surface 91 on the elongate member 74 supporting the lip 81 thereby swinging the elongate member 74 so that the vertical arm 62 is released therefrom. Once the vertical arm 62 is released the springs 95 urge the linear platform 16 upward from the position shown on the left hand side of FIG. 5 to the position shown on the right hand side of FIG. 5 under control of the piston 99. The tissue specimen 232 is then engaging the rotatable platform disc 113 with side 233 and also engaging on the opposite side 234 the linear platform disc 53. The specimen 232 is then in position to be frozen. Preferably, the surfaces 115 are pretreated with a non stick compound such as tetrafluoroethylene that is sold under the trademark Teflon.

The operator determines how many of the tissue specimen receiving sites represented by the discs 53 and 113 are being utilized. If only one or two are utilized then only the used two are selected for freezing by operation of the controller 228. Alternatively, if all four are to be utilized, the controller 228 is set for all four. Switch 230 and 231 are activated on the control panel 167 in order to respectively start one or both of the vacuum pumps 209 and 225. The valves 205, 206, 221 and 222 are open as necessary with the starting of their associated pumps 209 and 225. With reference to FIGS. 6 and 12, liquid nitrogen is drawn through the tubes 111 and 136 to the disc cavities 128 for distribution into the bores 127. The liquid nitrogen very rapidly cools the discs 53 and 113 and in particular cools the surfaces 115 thereof so that the tissue specimen 232 is very rapidly cooled from opposite sides thereof. Cooling in this manner freezes the tissue specimen 232 in a relatively very short time.

The liquid nitrogen preferably completely evaporates in the bores 127 so as to entirely transfer the enthalpy of evaporation thereof to the immediately surrounding discs 53 and 113 and at least partly to the tissue specimen 232. The gas from the evaporated liquid nitrogen travels radially outward along the bores 127 down through the channel 129 and into the larger bores 123 and 124 near the bottom of each disc 53 and 113. The evaporated gas is collected in the central chamber 125 and discharged through the passageway 120 into the tubes 135 and 108. The gas is drawn from the tubes 135 and 108 and transferred to the conduits 200 and 201. The gas in the conduits 200 and 201 is drawn by the vacuum pumps 209 and 225 respectively and discharged into the conduit 210 for return to the liquid nitrogen storage tank 184.

In this manner the vacuum pumps 209 and 225 both draw the gaseous nitrogen from the discs 53 and 113 thereby sucking or drawing liquid nitrogen into the discs 53 and 113 due to the vacuum created, but also discharge the return evaporated gas into the liquid nitrogen tank 184 under pressure so as to likewise pressurize the fluid in the tank 184 to act as a further propulsion force for driving the liquid nitrogen through the cryogenic fluid tubes 111 and 136. This quite effectively and very quickly provides sufficient liquid nitrogen flow at the discs 53 and 113 to very quickly freeze the tissue specimen 232.

Once this specimen 232 is frozen, the operator turns off the vacuum pumps 171, 179, 209 and 225 and rotates the rotatable platform 17 back to the open position thereof as is shown in FIG. 1. Tissue object holders are placed about the frozen specimen 232 in the manner described in my previous patents U.S. Pat. Nos. 4,695,339 and 4,752,347. The tissue specimen 232 is then removed and further procedures, such as sectioning in a cryostat, are performed on it. Upon returning the rotatable platform 17 to the open position thereof, the pin 88 engages the arm 62 to bias the arm 62 (the arm 62 is biased to the right as seen in FIG. 8) while the spring 75 biases the elongate member 74 towards the arm 62 to thus reposition the arm 62 behind the lip 81. The arm 62 is thereby locked into position and the linear platform 16 is drawn downwardly by this process and held in that position until the arm 62 is again released from the lip 81.

It is foreseen that in certain embodiments of the present invention, thermoelectric cooling modules could be substituted for the cryogenic fluid used to cool the disc 53 and 113.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for quick freezing tissue specimens for medical study comprising:
   a) a first platform having a first surface for receiving a specimen;
   b) a second platform having a second surface for operably engaging the specimen; said first and second platforms being rotatable relative to one another about a substantially horizontal axis between a first open position wherein the first and second platforms are sufficiently spaced to allow positioning of the specimen on said first platform surface such that said first and second platforms are facing substantially upwards and a second covering position wherein the second platform is positioned directly over said first platform and in spaced relationship thereto such that said first and second platforms are facing each other; and
   c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms are in facing relationship and engage the specimen with said respective first and second surfaces from opposite sides of the specimen.

2. The apparatus according to claim 1 wherein:
   a) each of said first and second platforms are operably connected to a cryogenic system in such a manner as to allow said cryogenic system to selectively reduce the temperature of said first and second surfaces, when in the engaging position thereof whereby the specimen is rapidly cooled from opposite sides thereof.

3. An apparatus for quick freezing tissue specimens for medical study comprising:
   a) a first platform having a first surface for receiving a specimen;
   b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;
   c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) each of said first and second platforms being operably connected to a cryogenic system in such a manner as to allow said cryogenic system to selectively reduce the temperature of said first and second surfaces, when in the engaging position thereof whereby the specimen is rapidly cooled from opposite sides thereof;

e) said first and second surfaces being associated with a first and a second disc supported by said first and second platforms respectively;

f) each of said discs having an internal chamber that is flow connected to said cryogenic system so as to receive cryogenic liquid in each of said chambers; and g) each of said discs chambers being flow connected to a gas conduit so as to allow evaporated cryogenic liquid to be conveyed from said chamber as a gas.

4. The apparatus according to claim 3 wherein:

a) each of said discs are generally cylindrical in shape and each of said chambers is radially centrally located in a respective disc; and b) each disc includes a plurality of radially extending bores extending from a respective chamber to near a periphery of a respective disc and in close proximity to a respective surface.

5. The apparatus according to claim 4 wherein:

a) each of said chambers is a distribution chamber and each of said bores is a liquid evaporation bore; and wherein each disc includes;

b) a collection chamber for collecting gas evaporated from said liquid and being located on the opposite side of a respective distribution chamber from a respective surface;

c) each disc also includes a plurality of radially extending gas collection bores flow connected to a respective collection chamber; and d) a conduit flow connecting said evaporation bores with said collection bores.

6. The apparatus according to claim 5 wherein:

a) each of said distribution chambers is connected by a respective nipple to a respective liquid delivery tube of said cryogenic system;

b) each of said collection chambers is connected by a respective nipple to a respective gas return tube; and c) each of said liquid delivery tubes is sleeved in and substantially smaller in diameter than an associated gas return tube.

7. The apparatus according to claim 3 wherein:

a) each of said discs are encircled by a channel adjacent the surface associated with an associated disc; and including b) a vacuum pump flow connected to each of said channels.

8. An apparatus for quick freezing tissue specimens for medical study comprising:

a) a first platform having a first surface for receiving a specimen;

b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;

c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) each of said first and second platforms being operably connected to a cryogenic system in such a manner as to allow said cryogenic system to selectively reduce the temperature of said first and second surfaces, when in the engaging position thereof whereby the specimen is rapidly cooled from opposite sides thereof;

e) a cryogenic liquid storage tank;

f) said cryogenic system including a liquid delivery tube flow connecting the liquid tank to each platform for cooling said surfaces;

g) a gas return tube flow connecting between said platforms and said tank; and h) a vacuum pump operably flow positioned along said return tube such that during operation of said vacuum pump, liquid is drawn from said tank to said platforms for cooling and evaporated gas is drawn from said platforms and returned to said tank to pressurize said tank such that liquid is urged from said tank both due to the vacuum pump drawing a vacuum on the return tube and by gas being returned to and pressurizing said tank.

9. An apparatus for quick freezing tissue specimens for medical study comprising:

a) a first platform having a first surface for receiving a specimen;

b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;

c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) said first platform being a rotating motion platform and said second platform being a linear motion platform; and b) a central rotating column; said column being joined to said rotating motion platform by an arm structure.

10. The apparatus according to claim 9 including:

a) a cryogenic conduit system operably connected to said rotating motion platforms and said linear motion platform;

b) said system including a liquid storage tank and at least one delivery tube for flow connecting said tank with each of said platforms respectively;

c) each of said delivery tubes for said rotating motion platform passing through an interior of said column.

11. The apparatus according to claim 10 wherein:

a) said column includes a cryogenic rotating junction whereat said delivery tubes for said rotating motion platform enter said column;

b) said junction comprising a first quartz tube that is non rotatable with said column and a second quartz tube slidebly and rotatably received relative to said first quartz tube and also being rotatable with said column; each of said delivery tubes for said rotating motion platform passing through said first and second quartz tubes.

12. The apparatus according to claim 11 wherein:

a) said first quartz tube is a central quartz tube receiving in opposite ends thereof said second quartz tube and a third rotatable quartz tube.

13. An apparatus for quick freezing tissue specimens for medical study comprising:

a) a first platform having a first surface for receiving a specimen;

b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;

c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) a side support panel located near one end of each of said first and second platforms; and e) a stop located on said side support panel; said stop having a first surface positioning said first platform when in the covering position thereof and said stop having a second surface positioning said second platform in a stop position when said second platform is in the specimen engaging position thereof.

14. The apparatus according to claim 13 wherein;

a) said stop includes an adjustable cam mechanism to selectively operably vary the stop position associated with said second platform.

15. An apparatus for quick freezing tissue specimens for medical study comprising:

a) a first platform having a first surface for receiving a specimen;

b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;

c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) frame structure connected to said second platform;

e) said linear movement mechanism being supported by said frame structure and connected to said second platform; and f) said second platform having an aperture therethrough; said linear movement mechanism including a post slidingly received in said aperture and allowing movement of said platform linearly along an axis associated with said post.

16. The apparatus according to claim 15 including:

a) a second aperture in said second platform; and b) a second post mounted on said frame structure and slideably received through said second aperture so as to allow linear motion of said second platform along an axis of said second post, but so as to prevent relative sidewise or angular motion of said second platform relative to said frame structure.

17. The apparatus according to claim 15 wherein:

a) said biasing device is a compression spring mounted about said post and biasing said second platform in the direction of said first platform when said first platform is in the covering position thereof.

18. The apparatus according to claim 15 including:

a) a dampener connected to said second platform and operably acting in cooperation with said biasing device to limit the velocity of the second platform toward the first platform when the first platform is in the covering position thereof.

19. An apparatus for quick freezing tissue specimens for medical study comprising:

a) a first platform having a first surface for receiving a specimen;

b) a second platform having a second surface for operably engaging the specimen; said first and second platforms being rotatable relative to one another between a first open position wherein the first and second platforms are sufficiently spaced to allow positioning of the specimen on said first platform surface and a second covering position wherein the second platform is positioned directly over said first platform and in spaced relationship thereto;

c) linear movement mechanism cooperating with said first and second platforms; said linear movement mechanism including a latch device to prevent linear movement until said second platform is in the covering position thereof and a linear biasing device for urging said first and second platform toward one another into a position wherein both of said first and second platforms engage the specimen with said respective first and second surfaces from opposite sides of the specimen;

d) a pivot bar pivotally mounted on said frame;

e) a first arm swingably connected to said second platform; and fixedly joined to said bar;

f) a second arm fixedly joined at one end to said bar and having a distal end; and g) a latch mounted on said frame and selectively engaging said second arm distal end such that, when engaged, said second platform is prevented from moving toward said first platform and when not engaged said second platform moves to the engaging position thereof.

20. The apparatus according to claim 19 wherein:

a) said latch device includes a trigger to release said latch when said first platform is in the covering position thereof.

21. The apparatus according to claim 20 wherein:

a) said latch device includes a reset mechanism that automatically resets the latch into the engaging position thereof when said first platform moves from the covering position thereof.

22. An apparatus for freezing a tissue specimen utilizing cryogenic fluids comprising:

a) a platform having a tissue specimen receiving surface; said platform being constructed of a heat transferable material in a region thereof near said surface; said platform including a chamber beneath said surface for receiving a cryogenic liquid;

b) a liquid tank for containing cryogenic liquid;

c) a liquid delivery tube having a first end flow connected to a liquid containing level of said tank and having a second end flow connected to said chamber;

d) a return tube flow connected to said chamber at one end and to said tank at an opposite end for returning gas evaporated from the cryogenic liquid to said tank;

e) a vacuum pump flow positioned along said return tube and being adapted to draw gas from said chamber to create a negative pressure therein to urge cryogenic liquid from said tank to said chamber and to return gas to said tank under pressure to help pressurize the liquid in said tank and thereby further urge liquid to flow from said tank through said delivery tube to said chamber.

23. The apparatus according to claim 22 wherein:

a) said platform includes a disc with said surface is located on said disc; and b) insulation positioned about said disc to at least partially insulate said disc from a remainder of said platform.

24. The apparatus according to claim 23 wherein:

a) said disc is cylindrical in shape and said surface is substantially planar.

25. The apparatus according to claim 23 wherein:

a) said chamber is centrally located relative to an axis of said disc; and including b) a plurality of distribution bores extending radially outward from said chamber in close proximately to said surface to near the radial outside of said disc.

26. The apparatus according to claim 24 wherein:

a) said chamber is a liquid receiving chamber; and including:

b) a gas collection chamber centrally located in said disc along the axis of said disc; said collection chamber being flow connected to said return tube and located in said disc in spaced relation from said receiving chamber on a side thereof opposite said surface;

c) a plurality of collection bores extending radially between said collection chamber and near the outside of said disc; and d) a conduit flow connecting said distribution bores with said collection bores near the outside of said disc.

27. The apparatus according to claim 26 wherein:

a) said conduit comprises a circumferential channel extending about said disc in spaced relation to said surface and flow communicating with said distribution bores and said collection bores; and b) said insulation comprises an insulative sleeve surrounding the radially outer surface of said disc; said sleeve covering said channel and operably cooperating with said channel to provide for flow of fluid between said distribution and collection bores.

28. The apparatus according to claim 26 wherein:

a) said receiving chamber is flow connected to said liquid delivery tube by a first nipple;

b) said collection chamber is flow connected to said return tube by a second nipple; and wherein c) said delivery tube is located within and is of substantially smaller diameter than said return tube.

29. The apparatus according to claim 22 wherein:

a) said liquid delivery tube is sized to be autoperfuseable for liquid nitrogen and has an interior diameter within the range of 0.051 and 0.074 inches.

30. The apparatus according to claim 22 including a) a holding tank flow connected to said return tube between said chamber and said vacuum pump.

31. The apparatus according to claim 22 including:

a) an operator operable flow control valve located in said return tube between said chamber and said vacuum pump.

32. In a machine utilizing cryogenic fluids for cooling and having a first portion that rotates about an axis relative to a second portion and further wherein the cryogenic liquid is conveyed between said first and second portions, the improvement wherein:

a) said cryogenic liquid passes through tubing having a rotary junction at a location of rotation;

b) said junction comprising a first quartz tube joined to said first portion and a second quartz tube joined to said second portion; said quartz tubes being sized such that one is sleeved in and slideably received within the other and such that both tubes have a common axis of rotation aligned with said axis so as to allow rotation of one of the tubes relative to the other when said first portion rotates relative to said second portion.

33. The machine according to claim 32 including:

a) a third quartz tube joined to said first portion and being rotatably received in said second quartz tube such that said first and third quartz tubes coaxially project from said second quartz tube.

34. The machine according to claim 32 including:

a) a liquid cryogenic delivery tube passing through said first and second quartz tubes.

35. The machine according to claim 33 wherein a) said second quartz tube includes a central aperture through a sidewall thereof; and including b) a quartz tail piece tube mounted in said aperture such that said quartz tubes collectively form a T-shaped junction.

36. The machine according to claim 35 including:

a) a T-shaped member formed of a plastic construction receiving said T-shaped junction and snugly engaging said second quartz tube so as to operably support said quartz T-shaped junction.

37. A cryogenic freezing platform for relatively quick freezing of a specimen placed on the platform; said platform comprising:
 a) a cylindrically shaped disc constructed of a relatively high heat transferable material; said disc having a generally planar surface adapted to receive a tissue specimen for freezing;
 b) said disc including first and second inner chambers;
 c) said first chamber being located in close proximity to said surface;
 d) said first chamber being adapted to flow connect to a source of cryogenic liquid;
 e) said second chamber being opposite said first chamber relative to said surface;
 f) said disc including a conduit for flow connecting between said first and second chambers; and
 g) said second chamber being adapted to be flow connected to a gas discharge tube.

38. A cryogenic freezing platform for relatively quick freezing of a specimen placed on the platform; said platform comprising:
 a) a cylindrically shaped disc constructed of a relatively high heat transferable material; said disc having a generally planar surface adapted to receive a tissue specimen for freezing;
 b) said disc including first and second inner chambers;
 c) said first chamber being located in close proximity to said surface;
 d) said first chamber being adapted to flow connect to a source of cryogenic liquid;
 e) said second chamber being opposite said first chamber relative to said surface;
 f) said disc including a conduit for flow connecting between said first and second chambers;
 g) said second chamber being adapted to be flow connected to a gas discharge tube;
 h) a plurality of distribution bores extending radially between said first chamber and near the radial exterior of said disc;
 i) a plurality of collection bores radially extending between said second chamber and near the outside of the disc; and
 j) said conduits flow connecting said collection bores with said distribution bores.

39. The platform according to claim 38 including:
 a) a cylindrical insulative sleeve snugly received on and extending circularly around the disc.

40. The platform according to claim 39 wherein:
 a) said conduit is constructed from cooperation between said sleeve and a circumferential channel about said disc flow communicating with each of said bores.

41. In an apparatus for treating a tissue specimen wherein said apparatus includes a platform having a surface thereon for receiving the specimen; the improvement comprising:
 a) a disc mounted in said platform and supporting said surface;
 b) a channel generally encircling said surface located in said platform;
 c) a sleeve constructed of insulative material generally surrounding said disc and operably located between said disc and said channel so as to insulate said disc from said channel; and including
 d) a vacuum pump flow connected to said channel so as to operably draw gases from said channel.

42. The apparatus according to claim 41 wherein:
 a) said disc and said surface are circular.

43. In an apparatus for treating a tissue specimen wherein said apparatus includes a platform having a surface thereon for receiving the specimen; the improvement comprising:
 a) a disc mounted in said platform and supporting said surface;
 b) a channel generally encircling said surface located in said platform;
 c) a vacuum pump flow connected to said channel so as to operably draw gases from said channel;
 d) said disc and surface are generally circular; and including:
 e) an insulating sleeve located between said disc and said channel;
 f) said channel being a first channel and said vacuum pump being a first vacuum pump; and
 g) a second channel closely spaced from said first channel and a second vacuum pump flow connected to said second channel operably drawing gases therefrom.

44. The apparatus according to claim 43 wherein:
 a) each of said channels is ring shaped and entirely surrounds said surface.

45. In an apparatus for treating a tissue specimen having a frame and a first platform for engaging the specimen, the improvement wherein:
 a) said first platform is a rotary motion platform pivotally connected to said frame; and including
 b) a linear motion platform; said rotary motion platform being positionable in a non covering position relative to said linear motion platform and being operably moveable to a covering position relative to said linear motion platform by rotating said rotary motion platform;
 c) said linear motion platform having at least first and second spaced positions relative to said rotary motion platform when the rotary motion platform is in the covering position thereof; said linear motion platform being closer to said rotary motion platform in said second position as compared to said first position; and
 d) a biasing mechanism for urging said linear motion platform between said first and second positions thereof without substantial lateral or angular motion.

46. The apparatus according to claim 45 including:
 a) a latch mechanism for operably preventing said linear motion platform from moving from said first position to said second position unless said rotary platform is in the covering position thereof; and
 b) said latch mechanism includes an automatic trigger to release said latch mechanism when said rotary motion platform is placed in the covering position thereof.

47. The apparatus according to claim 46 wherein:
 a) said latch mechanism includes an automatic reset mechanism to automatically reposition said linear motion platform in the first position thereof when said rotary motion platform is moved from the covering position thereof.

48. The apparatus according to claim 47 wherein said latch mechanism includes:
 a) a pivot bar pivotally connected to said frame;
 b) a first arm fixedly attached at one end thereof to said bar and swingably attached at the opposite end thereof to said linear motion platform;
 c) a second arm fixedly attached at a first end thereof to said bar and having a distal second end;

d) a latch swingably mounted on said frame and having a shoulder to receive said second arm distal end when in a latched position thereof and having a non latched position wherein said second arm distal end is not received by said shoulder;

e) a spring mechanism urging said latch from said unlatched to said latched position; and f) said biasing mechanism being free to urge said linear motion platform toward said rotary platform when said latch is in the unlatched position and being prevented from urging said linear motion platform toward said rotary platform when in the latched position thereof.

49. The apparatus according to claim 48 wherein:

a) said latch includes a cam surface, and including b) a cam follower connected to said rotary motion platform and urging said latch from the latched position to the unlatched position thereof when said rotary motion platform is in the covering position thereof.

50. The apparatus according to claim 49 wherein:

a) said reset mechanism includes a projection connecting to said rotary motion platform and operably engaging said second arm to urge the linear motion platform to the first position thereof and to replace the latch in the latched position thereof as said rotary motion platform moves from the covering position to the non covering position thereof.

51. A method of preparing a tissue specimen with a non planar side for slicing comprising the steps of:

a) placing the side of the specimen on a planar receiving surface;

b) covering the specimen with a flexible plastic sheeting;

c) withdrawing gas from between the sheeting and said receiving surface so as to draw said sheeting toward the surface and flatten against said receiving surface;

d) covering the specimen with a second covering surface;

e) cooling said receiving and covering surface so as to freeze said specimen utilizing cryogenic fluid to cool said specimen; and f) moving said covering surface into engagement with said specimen with substantially only a linear motion.

52. The method according to claim 51 including the step of:

a) while said receiving surface is cooling, simultaneously reducing the temperature of said second surface with cryogenic fluids so as to simultaneously cool and then freeze said specimen from opposite sides thereof.

* * * * *